United States Patent [19]

Haberman

[11] Patent Number: 4,554,912

[45] Date of Patent: Nov. 26, 1985

[54] PLASTIC ORTHOTIC THERAPEUTIC DEVICE

[76] Inventor: Louis J. Haberman, c/o Long Hill Medical Ctr., 9 Post Rd., Oakland, N.J. 07436

[21] Appl. No.: 571,821

[22] Filed: Jan. 18, 1984

[51] Int. Cl.⁴ .............................................. A61F 3/00
[52] U.S. Cl. ................... 128/80 E; 128/80 J
[58] Field of Search ............. 128/80 E, 80 R, 80 J, 128/80 H, 82, 83, 87 R

[56] References Cited

U.S. PATENT DOCUMENTS

| | | | |
|---|---|---|---|
| 114,669 | 5/1871 | Grant | 128/80 J |
| 1,656,322 | 1/1928 | Fischer | 128/80 J |
| 1,691,235 | 11/1928 | Fischer | 128/80 J |
| 3,916,886 | 11/1975 | Rogers | 128/80 E |
| 4,289,122 | 9/1981 | Mason et al. | 128/80 E |

*Primary Examiner*—John D. Yasko

*Attorney, Agent, or Firm*—Richard L. Miller

[57] ABSTRACT

A plastic orthotic therapeutic device which applied correcting pressure for varus or foot inversion and equinus or foot drop. This combination is prevalent in a condition known as spastic equinovarus which occurs with alarming frequency in post-stroke and brain injured patients. Equinus is controlled by a three pressure point system consisting of a foot plate, a broad proximal posterior section and the wearer's shoe. Varus is controlled by a three point pressure point system consisting of an appropriately relieved and padded malleolar area, a high medial wall, an extended projection proximal to medial malleolus, and an extended trim line over the first tarsal bone of the wearer. This orthosis is made of lightweight, hygienic polypropylene and may be worn inside the patient's shoe. It is easily donned and doffed using only one hand.

7 Claims, 5 Drawing Figures

PLASTIC ORTHOTIC THERAPEUTIC DEVICE

BACKGROUND OF THE INVENTION

The present invention relates generally to orthotic devices which may be worn by persons with certain disorders. Persons suffering with neurological disorders occurring from cerebral vascular accidents and brain trauma often develop marked deformities in the lower and upper extremities. The present invention addresses lower limb involvement only.

In many instances, the deformity that results is classified as Spastic Equinovarus. Spacticity, and its accompanying deformity of the lower limb severely reduces the ambulatory capacity of its victims. This deformity of the foot/ankle complex has traditionally been most difficult to correct via orthotic devices, physical medicine and medications.

The two components of Spastic Equinovarus, the equinus or foot drop and the varus or foot inversion must be treated by use of a single orthosis. Mason, et al. (U.S. Pat. No. 4,289,122) invented an orthosis which addresses the equinus deforming forces by means of a grave and sole plate but does not correct for varus or foot inversion. Likewise, Bronkhorst (U.S. Pat. No. 4,351,3240) invented a therapeutic walking device which cannot prevent varus or foot inversion and would also be uncomfortable to wear since it is not fitted to the contour of the wearer's foot.

SUMMARY OF THE PRESENT INVENTION

It is, therefore, the primary object of the present invention to provide a plastic orthotic therapeutic device which corrects for both varus and equinus deforming forces simultaneously. Spastic equinovarus occurs with alarming frequency in post-stroke and brain injured patients. Spastic equinovarus can manifest itself mildly, moderately or severely. It is the intent of the present invention to provide relief for the various states of the dysfunction. Its outer limits of correction occurs when the foot/ankle complex is in a fixed state of equinovarus.

Another object is to have the invention apply two distinct yet complimentary three point pressure systems to the involved limb. One set of forces effectively controls the equinus or drop foot deformity. Another set corrects the varus or foot inversion component of the deformity.

A further object is to provide a comfortable orthosis. The orthosis is a total contact system requiring a highly intimate fit at all times.

A further object is to provide a lightweight, hygienic and cosmetic orthosis. This is accomplished by fabricating the device from orthopedic grade polypropelene plastic which is flesh toned and stress relieved. It is formed over a positive plaster model of a patient's leg at 400 degrees Farenheit under a vacuum of 25–30 pounds.

A yet further object is to allow this orthosis to be donned and doffed with ease by the patient using only one hand.

As significant reduction and/or elimination of the spastic response in the foot ankle complex takes place, it has been observed that knee, hip and upper limb spasticity is also reduced; thus improving the total rehabilitation of the patient beyond what was anticipated.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows.

DETAILED DESCRIPTION OF THE PREFERRED EMBODIMENT

Figure 1:
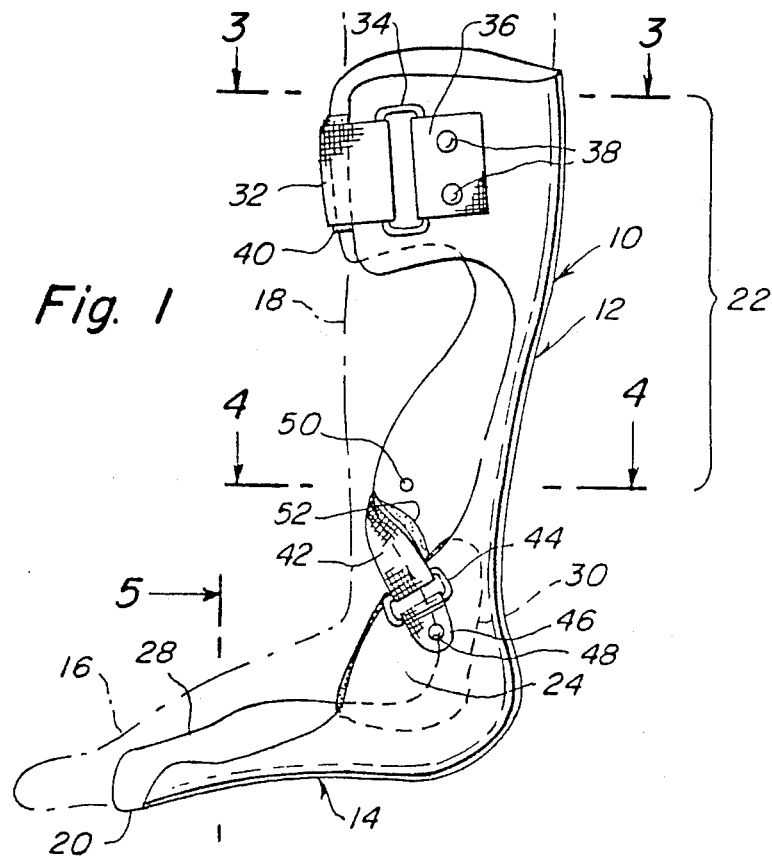
FIG. 1 is a side perspective view of the invention illustrated typically for a left foot.
Figure 3:
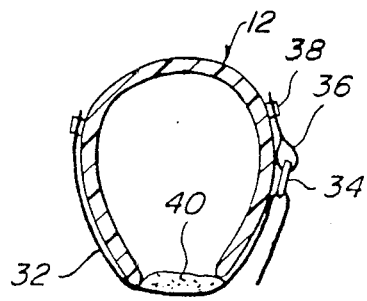
FIG. 3 is a partial cross sectional view taken on line 3—3 in FIG. 1.
Figure 4:
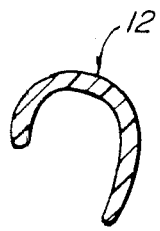
FIG. 4 is a partial cross sectional view taken on line 4—4 in FIG. 1.
Figure 5:
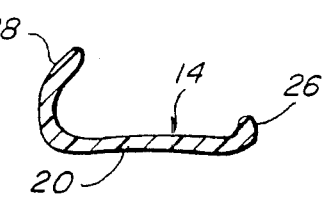
FIG. 5 is a partial cross sectional view taken on line 5—5 in FIG. 1.
Figure 2:
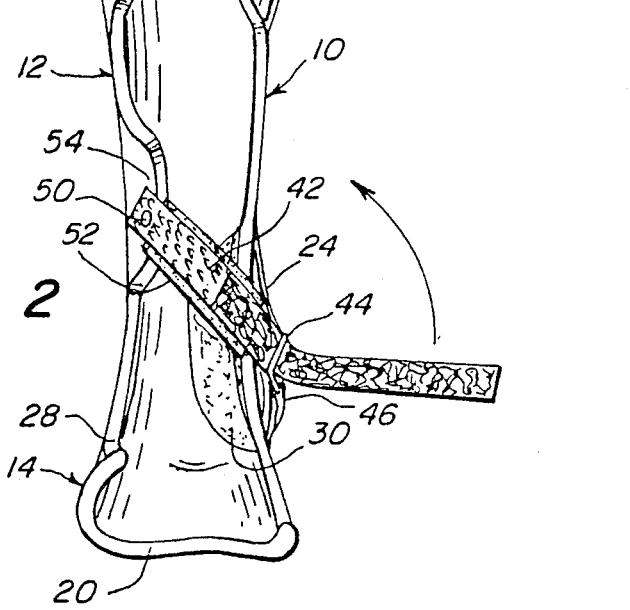
FIG. 2 is a front perspective view of the invention also for the left foot.

The plastic orthotic therapeutic device 10 in FIGS. 1 and 2 consists of two main components a greave or leg section 12 and a plantar or leg section 14. Both sections are contoured to the wearer's foot by means of a molding process in which a polypropylene sheet is vacuum formed to positive mold of the wearer's foot and leg. Foot 16 and leg 18, shown in dashed lines, are in intimate contact with plantar section 14 and greave section 12.

In order to prevent foot drop or equinus, the wearer's foot 16 is prevented from moving in a downward direction by a foot plate 20, broad proximal posterior section 22 and the wearer's shoe. This provides a three pressure point system.

In order to prevent varus or foot inversion, the wearer's foot 16 is prevented from rotating inward by an appropriately relieved malleolar area 24, a high medial wall 26, an extended projection proximal to medial malleolus 54, and an extended trim line 28 over the first tarsal bone of the wearer. The inner surface of the relieved malleolar area has padding 30.

The plastic orthotic therapeutic device is secured to the wearer's leg by means of a hook and loop pile fastener shin strap 32 and associated buckle 34, buckle securing strap 36 and rivets as typified by 38. In order to prevent chafing a shin pad 40 is provided.

To further secure the invention to the wearer's foot 18 just above the ankle joint, an optional lower hook and loop pile fastener ankle strap with associated buckle 44, buckle securing strap 46, rivets typified by 48 and 50 and a lower strap pad 52 may be added.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A plastic orthotic therapeutic device comprising in combination greave or leg section, a plantar or foot section, said greave or leg section and said plantar or foot section being integral and rigidly formed of unitary construction, means for providing forces to correct the deforming components of equinus or foot drop, simultaneous means for providing forces to correct the deforming components of varus or foot inversion, means for providing for comfort to a wearer when said plastic orthotic device is worn and means for allowing the wearer of said orthotic device to easily don and doff said device, wherein said means for providing forces to correct the deforming components of equinus or foot drop consist of a three point pressure system including a foot plate, a broad proximal posterior section, and the shoe of the wearer, and wherein said means for providing forces to correct the deforming components of varus or foot inversion consist of a three point pressure system including an appropriately relieved malleolar area, a high medial wall, an extended projection proximal to the medial malleolus, and an extended trim line over the first tarsal bone of said wearer.

2. A plastic orthotic therapeutic device, as recited in claim 1, wherein said greave or leg section is molded out of a thermally moldable yet rigid material in such manner as to fit the leg and calf contour of said wearer.

3. A plastic orthotic therapeutic device, as recited in claim 1, wherein said plantar or foot section is molded out of a thermally moldable yet rigid material in such manner as to fit the foot of said wearer.

4. A plastic orthotic therapeutic device, as recited in claim 1, wherein said means for providing for comfort to said wearer when said plastic orthotic therapeutic device is worn consists of padding a relieved malleolar area and padding all attachment hood and loop pile fastener straps.

5. A plastic orthotic therapeutic device, as recited in claim 1, wherein said means for allowing the wearer of said orthotic device to easily don and doff said device consists of at least one hook and loop pile fastener strap and means for securing said strap so that orthotic device remains fixedly in place when said wearer walks.

6. A plastic orthotic therapeutic device as recited in claim 5, wherein said means for securing said strap consists of riveting said strap to an appropriate place on said orthotic device and providing a matching buckle which is mounted to an opposing appropriate connection point.

7. A plastic orthotic therapeutic device, as recited in claim 5, wherein said hook and loop pile fastener strap and said means for securing said strap are located near the top of said plantar or foot section.

* * * * *